US010522298B2

United States Patent
Eidelman et al.

(10) Patent No.: US 10,522,298 B2
(45) Date of Patent: Dec. 31, 2019

(54) METHODS OF MANUFACTURING A HERMETICALLY SEALED WET ELECTROLYTIC CAPACITOR AND A HERMETICALLY SEALED WET ELECTROLYTIC CAPACITOR

(71) Applicant: Vishay Sprague, Inc., Bennington, VT (US)

(72) Inventors: Alex Eidelman, Beer-Sheva (IL); John Evans, Pownal, VT (US); Stephen Breithaupt, N. Bennington, VT (US); Sarah Lastella, Troy, NY (US); Edward Fairfield, Hopkinton, NH (US); Ilia Skatkov, Beer-Sheva (IL); Vicki Segel, Beer-Sheva (IL); Pavel Vaisman, Beer-Sheva (IL); Hila Eshel, Beer-Sheva (IL)

(73) Assignee: Vishay Sprague, Inc., Bennington, VT (US)

( * ) Notice: Subject to any disclaimer, the term of this patent is extended or adjusted under 35 U.S.C. 154(b) by 0 days.

(21) Appl. No.: 15/462,268

(22) Filed: Mar. 17, 2017

(65) Prior Publication Data
US 2017/0194099 A1 Jul. 6, 2017

Related U.S. Application Data

(63) Continuation of application No. 12/759,769, filed on Apr. 14, 2010, now abandoned.
(Continued)

(51) Int. Cl.
*H01G 9/10* (2006.01)
*H01G 9/00* (2006.01)
(Continued)

(52) U.S. Cl.
CPC ............. *H01G 9/10* (2013.01); *A61N 1/3975* (2013.01); *H01G 9/008* (2013.01);
(Continued)

(58) Field of Classification Search
CPC .......... H01G 9/10; H01G 9/145; H01G 9/035; H01G 9/0029; H01G 9/008; H01G 9/012
See application file for complete search history.

(56) References Cited

U.S. PATENT DOCUMENTS 3,763,409 A * 10/1973 Sheard ................. H01G 4/0085
106/1.13
4,780,797 A 10/1988 Libby
(Continued)

FOREIGN PATENT DOCUMENTS

CN 101271769 A 9/2008
CN 101271772 A 9/2008
(Continued)

*Primary Examiner* — David M Sinclair
(74) *Attorney, Agent, or Firm* — Volpe and Koenig, P.C.

(57) ABSTRACT

Methods of manufacturing a hermetically sealed wet electrolytic capacitor and a hermetically sealed wet electrolytic capacitor are described. A method of manufacturing a wet electrolytic capacitor includes forming a cathode of the capacitor by forming a case comprising a metal substrate, the metal substrate having an alloyed surface, depositing a smooth film comprising palladium and copper as a tacking layer on the alloyed surface of the metal substrate, and depositing a rough, high surface area layer on the tacking layer to achieve a high capacitance cathode. A first terminal is electrically connected to the cathode. An anode is formed. A second terminal is electrically connected to the anode. An electrolytic solution is disposed within the case, and the case is hermetically sealed.

19 Claims, 1 Drawing Sheet

Related U.S. Application Data

(60) Provisional application No. 61/169,764, filed on Apr. 16, 2009.

(51) Int. Cl.
| | |
|---|---|
| *H01G 9/012* | (2006.01) |
| *A61N 1/39* | (2006.01) |
| *H01G 9/008* | (2006.01) |
| *H01G 9/035* | (2006.01) |
| *H01G 9/145* | (2006.01) |

(52) U.S. Cl.
 CPC ........... *H01G 9/0029* (2013.01); *H01G 9/012* (2013.01); *H01G 9/035* (2013.01); *H01G 9/145* (2013.01)

(56) References Cited

U.S. PATENT DOCUMENTS

| | | | |
|---|---|---|---|
| 4,942,500 A | 7/1990 | Libby | |
| 5,043,849 A | 8/1991 | Libby | |
| 5,334,219 A | 8/1994 | Kroll | |
| 5,607,454 A | 3/1997 | Cameron et al. | |
| 5,621,608 A | 4/1997 | Arai et al. | |
| 5,926,362 A | 7/1999 | Muffoletto et al. | |
| 6,334,879 B1 | 1/2002 | Muffoletto et al. | |
| 6,522,524 B1 | 2/2003 | Feger et al. | |
| 6,599,580 B2 * | 7/2003 | Muffoletto ........... C23C 14/5833 427/250 | |
| 6,687,117 B2 | 2/2004 | Liu et al. | |
| 6,743,370 B1 * | 6/2004 | Feger ................ H01G 9/035 252/62.2 | |
| 6,761,728 B2 | 7/2004 | Harguth et al. | |
| 6,801,424 B1 | 10/2004 | Nielsen et al. | |
| 6,819,544 B1 | 11/2004 | Nielsen et al. | |
| 6,965,510 B1 | 11/2005 | Liu et al. | |
| 7,169,284 B1 | 1/2007 | Jiang et al. | |
| 2002/0067589 A1 * | 6/2002 | Marshall ................ H01G 9/022 361/503 | |
| 2004/0211043 A1 * | 10/2004 | Will ........................ H01G 9/00 29/25.03 | |
| 2004/0240149 A1 | 12/2004 | Lessner et al. | |
| 2005/0077342 A1 | 4/2005 | Chen et al. | |
| 2005/0177193 A1 | 8/2005 | Nielsen et al. | |
| 2005/0180094 A1 * | 8/2005 | Muffoletto ............ H01G 9/035 361/504 | |
| 2005/0219787 A1 | 10/2005 | Stevenson | |
| 2006/0198082 A1 * | 9/2006 | Eberhard ................ H01G 9/04 361/516 | |
| 2006/0279907 A1 | 12/2006 | Doffing et al. | |
| 2008/0068779 A1 * | 3/2008 | Restorff ................... H01G 9/02 361/508 | |
| 2008/0232029 A1 | 9/2008 | Ning | |
| 2008/0232032 A1 | 9/2008 | Jones et al. | |
| 2010/0268292 A1 | 10/2010 | Eidelman et al. | |
| 2012/0179217 A1 * | 7/2012 | Bates .................... B22F 1/0055 607/5 | |

FOREIGN PATENT DOCUMENTS

| | | | |
|---|---|---|---|
| EP | 1053763 A2 | 11/2000 | |
| GB | 2447726 A | 9/2008 | |
| JP | H02-280310 A | 11/1990 | |
| JP | H05-114680 A | 6/1993 | |
| JP | 07254532 A * | 10/1995 | ............ H01L 24/48 |
| JP | H08-509385 A | 10/1996 | |
| JP | H10-312936 A | 11/1998 | |
| JP | 2003-265627 A | 9/2003 | |
| JP | 2007-526008 A | 9/2007 | |
| JP | 2008-235895 | 10/2008 | |
| WO | 94/00193 A1 | 1/1994 | |
| WO | 2005-001997 A2 | 1/2005 | |

* cited by examiner

METHODS OF MANUFACTURING A HERMETICALLY SEALED WET ELECTROLYTIC CAPACITOR AND A HERMETICALLY SEALED WET ELECTROLYTIC CAPACITOR

This application is a continuation of U.S. patent application Ser. No. 12/759,769, filed Apr. 14, 2010, which claims the benefit of U.S. Provisional Patent Application No. 61/169,764, filed on Apr. 16, 2009.

FIELD OF THE INVENTION

The present invention relates to capacitors, and more specifically to a capacitor suitable for use in medical applications such as implantable cardioverter defibrillators.

BACKGROUND

Capacitors are used in a wide range of electronic applications. Certain applications require a capacitor which is capable of a rapid electrical charge to a pre-determined voltage and, once charged, is also capable of delivering sizeable pulses of energy. One example of such an application is in implantable devices. In such an application, it is also important that the capacitor be compact in size and highly reliable.

Thus, what is needed is a capacitor suitable for use in applications, such as implantable cardioverter defibrillators, where reliability and performance are provided in a small size.

SUMMARY

Therefore, it is a primary object, feature, or advantage of the present invention to improve over the state of the art.

It is a further object, feature, or advantage of the present invention to provide a capacitor suitable for use in implantable devices.

A still further object, feature, or advantage of the present invention is to provide a capacitor that is capable of a rapid electrical charge to a pre-determined voltage and, once charged, is also capable of delivering sufficient pulses of energy to restore the normal function of a patient's heart when used in implantable cardioverter defibrillators (ICD).

Another object, feature, or advantage of the present invention is to provide a capacitor which is efficiently constructed and shaped to fit into the limited volume available within an ICD.

Yet another object, feature, or advantage of the present invention is to provide a capacitor with high performance and high reliability.

One or more of these and/or other objects, features, or advantages of the present invention will become apparent from the specification and claims that follow.

According to one aspect of the present invention, a hermetically sealed wet electrolytic capacitor is provided. The capacitor has a hermetically sealed case that encloses a cathode, an anode, an electrical insulator between the anode and the cathode and an electrolytic solution. A first terminal is electrically connected to the anode and a second terminal electrically connected to the cathode. The hermetically sealed wet electrolytic capacitor is able to provide a pulse delivery equal to at least 80 percent of the stored energy.

According to another aspect of the present invention, the capacitor's cathode includes a metal substrate having an alloy layer formed with a noble metal and a noble metal/base metal electrode element layer electrochemically deposited thereon, and the electrolytic solution has a conductivity between 10 and 60 mS/cm.

According to another aspect of the present invention, a method of manufacturing a capacitor is provided. The method includes hermetically sealing a case containing an electrolytic solution having a conductivity between 10 and 60 mS/cm. The method further includes electrically connecting a first terminal to an anode, the anode being insulated from a cathode. The method further includes electrically connecting a second terminal to the cathode. The cathode is formed from a metal substrate having an alloy layer formed with a noble metal and a noble metal/base metal electrode element layer electrochemically deposited thereon.

DETAILED DESCRIPTION OF THE PREFERRED EMBODIMENT

The present invention is now described with respect to a particular embodiment. That which is shown is merely for purposes of illustration and example, and one skilled in the art will understand that the present invention contemplates other options, alternatives, or variations.

Figure 1:
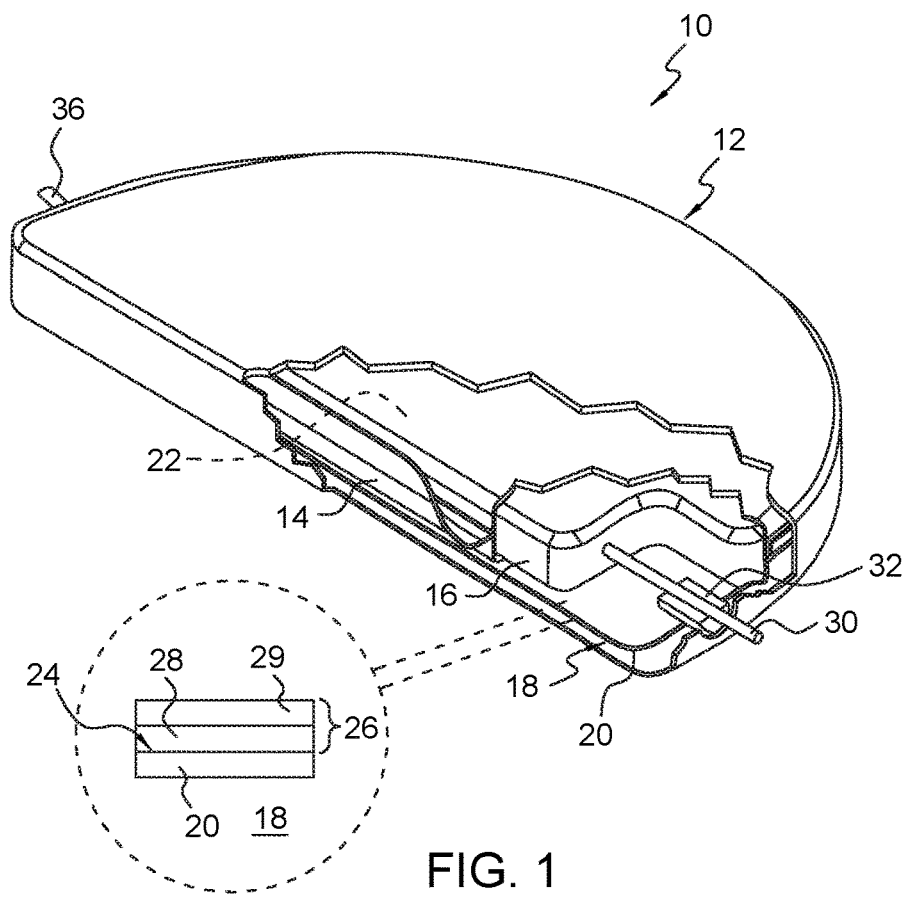
FIG. 1 illustrates one embodiment of a hermetically sealed wet electrolytic capacitor.

FIG. 1 illustrates one embodiment of a capacitor 10 of the present invention. Although shown in a semi-circle shape, the capacitor 10 need not have such a shape. This particular shape is merely an example. In FIG. 1, a hermetically sealed wet electrolytic capacitor 10 is shown. The capacitor 10 has a hermetically sealed case 12. The capacitor 10 has a cathode 18 and an anode 16. One example design for an anode 16 would comprise sodium reduced capacitor grade tantalum powder pressed to a green density of between 5.0 and 7.0 grams/cc then vacuum sintered between 1450° C. and 1650° C. Powder, press and sinter conditions may be varied to attain the requisite capacitance. Formation of the anode should be in an electrolyte capable of sustaining the voltage necessary for the required oxide thickness.

An insulator 14, (preferably, but not required, comprising one or more layers of a polymeric material), is positioned between the anode 16 and the cathode 18 to electrically insulate the anode 16 from the cathode 18. An electrolytic solution 22 is disposed within the hermetically sealed case 12 and surrounds both the cathode 18 and the anode 16. The electrolytic solution 22 preferably comprises a gel which includes DI water, organic and inorganic acids and an organic solvent. The constituent components of the electrolytic solution 22 may be admixed in a variety of concentrations to provide conductivity within a preferred range between 10 and 60 mS/cm. One example of such an electrolytic solution 22 would be:

65-80% DI water
0.2-0.6% phosphoric acid
15-30% ethylene glycol
3-6% oxalic acid
2-4% boric acid The cathode 18 is formed from a metal substrate 20 having an alloy layer 24 formed with a noble metal and a noble metal/base metal electrode element layer 26 electrochemically deposited on the alloyed surface from a solution of the metal salts. One example design for the cathode 18 may be a mixture of Pd and Cu electrodeposited on a Ti—Pd alloy. To increase adhesion of the cathode 18 to the alloyed substrate, an initial smooth film of Pd—Cu may be electrodeposited as a tacking layer 28. A rough, high surface area layer 29 can then be deposited on top of the tacking layer to achieve a high capacitance cathode 18.

The metal substrate 20 of the cathode 18 can be formed of a valve metal. Examples of such valve metals include tantalum, niobium, hafnium, vanadium, zirconium, titanium or any of their alloys. The metal substrate 20 may have any number of shapes or configurations, including a planar or cylindrical shape. The metal substrate 20 may be a liner of any suitable shape and may represent a part of the capacitor case 12. Such a construction of the cathode 18 results in high cathode capacitance which assists in efficiently delivering energy stored in the capacitor 10 to a load.

A first terminal 30 is shown extending through a spacer 32. The first terminal 30 is electrically connected to the anode 16. A second terminal 36 is electrically connected to the cathode 18.

Figure 2:
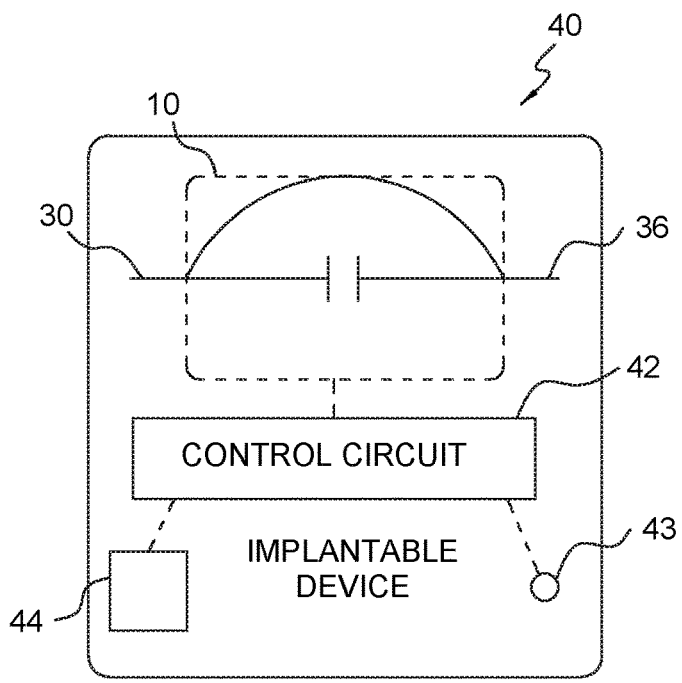
FIG. 2 illustrates the capacitor of FIG. 1 placed in an implantable cardioverter defibrillator.

FIG. 2 illustrates one embodiment of an implantable cardioverter defibrillator (ICD) device 40. The device 40 includes the capacitor 10 of FIG. 1 (with a first terminal 30 and a second terminal 36), and a control circuit 42, which is electrically coupled to the capacitor 10, a detector 43 and a battery 44. The capacitor 10 is configured to provide a pulse delivery of at least 80 percent, (but preferably greater than 87 percent), of stored energy between the first and second terminals 30, 36. The detector 43 monitors a patient's condition and provides this patient data to the control circuit 42. The control circuit 42 monitors the information from the detector and upon detection of an anomaly or a critical condition, (which may be defined as one or more predetermined parameters that have exceeded one or more predetermined thresholds).

By way of example, the detector 43 may detect electrical activity in the heart of a patient and forward this data to the control circuit 42. The control circuit 42 monitors this electrical activity and if it drops below a certain electrical level, or if the electrical activity becomes irregular (as happens with an arrhythmia), initiates delivery of an electrical shock.

The battery 44 may be used to charge the capacitor 10 and to power the ICD device. The charging of the capacitor 10 may be constant (to counter the effects of charge leakage), such that the capacitor 10 is always ready for discharge; may be periodic (i.e. charging at predetermined intervals to keep the charge level of the capacitor 10 above a predetermined threshold); or may be on demand, such that when the onset of an anomaly is detected, the battery 44 is used to charge the capacitor at that time.

In the application of an ICD device 40, the capacitor 10 performs the function of delivering electrical shock therapy into the heart of a patient when a control circuit 42 of the ICD device 40 detects an anomaly or a critical condition in the patient. The capacitor 10 allows the capacitor to be capable of providing a rapid electrical charge to a predetermined voltage, and thereafter delivering one or more pulses of sufficient energy to restore normal functions of a patient's heart.

The capacitor 10 as shown in FIG. 1 is efficient in nature and highly compact such that the capacitor 10 is constructed and shaped to fit within a limited volume within an ICD device 40. Preferably, the size of the capacitor 10 is 1.5-3.0 CC, and comprises a half-moon shape as shown in FIG. 1, although this should not be construed to be limiting to the present invention. The capacitor 10 is able to conform to any size and shape in order to fit the particular configuration demanded by the person within which it is being implanted.

In order to support the application of an ICD device 40, the capacitor 10 is able to supply a minimum of 9 J, (but preferably 12 J), upon demand. The amount of energy actually delivered is determined by the control circuit 42.

A hermetically sealed wet electrolytic capacitor has been described. The present invention is not to be limited to the specific embodiment shown or described herein as the present invention contemplates variations in the size and shape of the capacitor, variations in the materials used, and other variations, alternatives, and options as would be apparent to one skilled in the art.

What is claimed is:

1. A method of manufacturing a hermetically sealed wet electrolytic capacitor, the method comprising:
    forming a cathode of the capacitor by:
        forming a case comprising a metal substrate, the metal substrate being formed from a valve metal and having a titanium and palladium alloyed surface,
        depositing a smooth film comprising palladium and copper as a tacking layer on the alloyed surface of the metal substrate,
        depositing a rough layer on the tacking layer to achieve a high capacitance cathode;
    electrically connecting a first terminal to the cathode;
    forming an anode;
    electrically connecting a second terminal to the anode;
    disposing an electrolytic solution within the case; and
    hermetically sealing the case.

2. The method of claim 1, further comprising: positioning an insulator between the cathode and the anode.

3. The method of claim 1, wherein the metal substrate comprises a titanium alloy.

4. The method of claim 1, further comprising forming the anode from sodium reduced capacitor grade tantalum powder pressed to a green density of between 5.0 and 7.0 grams/cc and then vacuum sintered between 1450 degrees Celsius and 1650 degrees Celsius.

5. The method of claim 1, wherein the electrolytic solution has conductivity between 10 and 60 mS/cm.

6. The method of claim 1, wherein the electrolytic solution comprises water, inorganic acids, an organic acid and an organic solvent.

7. A hermetically sealed wet electrolytic capacitor comprising:
    a hermetically sealed capacitor case comprising a multi-layer cathode, the multi-layer cathode comprising:
        a metal substrate formed from a valve metal and having a titanium and palladium alloyed surface layer,
        a smooth film comprising palladium and copper deposited on the alloyed surface layer as a tacking layer, and
        a rough layer deposited on the tacking layer and configured to achieve high capacitance;
    an anode disposed in the hermetically sealed capacitor case; and
    an electrolytic solution disposed in the hermetically sealed capacitor case.

8. The hermetically sealed wet electrolytic capacitor of claim 7, further comprising:
    an insulator disposed between the cathode and the anode.

9. The hermetically sealed wet electrolytic capacitor of claim 7, wherein the metal substrate comprises a titanium alloy.

10. The hermetically sealed wet electrolytic capacitor of claim 7, wherein the anode comprises sodium reduced capacitor grade tantalum powder pressed to a green density of between 5.0 and 7.0 grams/cc and then vacuum sintered between 1450 degrees Celsius and 1650 degrees Celsius.

11. The hermetically sealed wet electrolytic capacitor of claim 7, wherein the electrolytic solution has conductivity between 10 and 60 mS/cm.

12. The hermetically sealed wet electrolytic capacitor of claim 7, wherein the electrolytic solution comprises water, inorganic acids, an organic acid and an organic solvent.

13. A method of manufacturing a hermetically sealed wet electrolytic capacitor, the method comprising:
providing a case formed from a valve metal having a titanium and palladium alloyed inner surface;
forming a cathode on the alloyed inner surface of the case, the cathode comprising multiple layers, at least one of the cathode layers comprising a smooth film comprising palladium and copper as a tacking layer deposited on the alloyed inner surface of the case;
disposing an anode within the case,
electrically connecting a first terminal to an anode, the anode being insulated from the cathode;
electrically connecting a second terminal to the cathode;
disposing an electrolytic solution within the case; and
hermetically sealing the case;
wherein the amount of energy delivered by the capacitor is greater than 87 percent of the stored energy of the capacitor.

14. The method of claim 13, further comprising preparing the electrolytic solution by admixing DI water, phosphoric acid, ethylene glycol and boric acid.

15. The method of claim 13, wherein the step of forming the cathode comprises depositing a layer on the tacking layer, wherein the layer has a rough surface.

16. The method of claim 13, further comprising: positioning an insulator between the cathode and the anode.

17. The method of claim 13, wherein the alloyed inner surface comprises a titanium alloy.

18. The method of claim 13, further comprising forming the anode from sodium reduced capacitor grade tantalum powder pressed to a green density of between 5.0 and 7.0 grams/cc and then vacuum sintered between 1450 degrees Celsius and 1650 degrees Celsius.

19. The method of claim 13, wherein the electrolytic solution has conductivity between 10 and 60 mS/cm.

* * * * *